United States Patent [19]

Hagins et al.

[11] Patent Number: 4,940,896
[45] Date of Patent: Jul. 10, 1990

[54] PYROELECTRIC CALORIMETER

[75] Inventors: William A. Hagins, Chevy Chase; Shuko Yoshikami, Bethesda, both of Md.

[73] Assignee: The United States of America as represented by the Department of Health and Human Services, Washington, D.C.

[21] Appl. No.: 305,331

[22] Filed: Feb. 2, 1989

[51] Int. Cl.$^5$ ............................................... G01J 1/00
[52] U.S. Cl. .................................................. 250/338.3
[58] Field of Search ..................................... 250/338.3

[56] References Cited

U.S. PATENT DOCUMENTS

| | | | |
|---|---|---|---|
| 3,935,485 | 1/1976 | Yoshida et al. | 310/338 |
| 3,970,862 | 7/1976 | Edelman et al. | 307/400 |
| 4,090,212 | 5/1978 | Byatt et al. | 357/24 |
| 4,115,692 | 9/1978 | Balcerak et al. | 250/338.3 |

OTHER PUBLICATIONS

Kynar Piezo Film publication, undated.
Hagins, W. A. et al, "Transduction Heats in Retinal Rods: Tests of the Role of cGMP by Pyroelectric Calorimetry", Proc. Natl. Acad. Sci. USA, vol. 86, pp. 1224-1228, Feb. 1989.
Marcus, Michael A., "Ferroelectric Polymers and Their Applications", Research Laboratories, Eastman Kodak Company, Rochester, NY 14650, U.S.A., Oct. 1981.
Tasaki, I. and Iwasa, K., "Temperature Changes Associated with Nerve Excitation: Detection by Using Polyvinylidene Fluoride Film", vol. 101, No. 1, 1981, pp. 172-176, Biochem. & Biophysic. Res. Comm.
Power, Joan F. and Mandelis, Andreas, "Photopyroelectric Thin-Film Instrumentation and Impulse-Response Detection. Part III: Performance & Signal Recovery Techniques", Rev. Sci. Instrum. 58(11), Nov. 1987, pp. 2032-2043.
Power, Joan F. and Mandelis, Andreas, "Photopyroelectric Thin-Film Instrumentation and Impulse-Response Detection. Part I: A Theoretical Model", Rev. Sci. Instrum. 58(11), Nov. 1987, pp. 2018-2032.
Roundy, C. B., SPIE Infra Red Technology 62: 191-8 (1975).
Lines, M. E. and Glass, Principles and Applications of Ferroelectrics and Related Materials, Clarendon Press, Oxford (1977), Chapters 1 and 5 and pp. 553-662.
Special Issue of the Journal Ferroelectrics, Nos. 1, 2, 3 and 4 (1980).
G. Gerlitczy et al., "Solef PVDF Biaxially Oriented Piezo- and Pyro Electric Films for Transducers", Sensors and Actuators, 12 (1987) 207-223.

Primary Examiner—Constantine Hannaher
Assistant Examiner—J. Eisenberg
Attorney, Agent, or Firm—Lowe, Price, LeBlanc, Becker & Shur

[57] ABSTRACT

A pyroelectric detector comprises a support member having a tapered through-hole therein, a first polyester film positioned on said support member, across said through-hole, an aluminum foil member located on an opposite side of said polyester film from said support member, a pyroelectric film located on an opposite side of said aluminum foil member from said first polyester film, at least one additional polyester film located on an opposite side of said pyroelectric film from said aluminum foil member, and two pyroelectrical leads connected to opposite sides of said pyroelectric film.

8 Claims, 7 Drawing Sheets

PYROELECTRIC CALORIMETER

TECHNICAL FIELD

The present invention relates to a method and apparatus useful for determining the heat capacity and heat conductivity of small samples of solids and liquids. In particular, the present invention relates to a microcalorimeter having an improved sensitivity and response speed for milligram samples based on the pyroelectric effect.

BACKGROUND ART

Conventional chemical calorimeters have been used to measure temperature changes of more than 20 microdegrees in liquid and solid samples weighing 100 milligrams or more with arrays of thermocouple elements surrounding the sample. To speed the detection of the heat, it is usually conducted as a measured heat flux through arrays of thermoelectric elements whose outputs are integrated and recorded. Small samples and small temperature changes are difficult to measure in this way because the thermocouples are brittle semiconductors that are hard to miniaturize.

Thermopiles made of conventional metal wires have been used to study heat changes in nerves and muscles. In these, an array of as many as 100 thermoelectric junctions are pressed against the tissue with thin sheets of mica as electrical and chemical barriers. The thinness of the mica makes the thermopile responses as fast as 10 milliseconds, but the low source impedances and thermoelectric powers of the thermocouples require that the signals be recorded with galvanometers of poor frequency response. Nevertheless, by signal averaging many responses of nerves with such systems, temperature changes of 7–10 microdegrees C. have been seen.

In 1981, I. Tasaki and K. Iwasa (Biochem. Biophys. Res. Commun. 101. 172–176(1981)) described a new and much more sensitive temperature sensor based on pyroelectric charge displacements in the artificial plastic film polymer, poly(vinylidene 1,1-difluoride). This polymer, PVDF, when coated with aluminum or nickel films and then stretched and heated in a strong electrical field becomes a permanently polarized dielectric material with a very high insulation resistance. When subjected to a temperature change of 1 degree K., PVDF films 9–10 micrometers thick show potential changes between their two surfaces of as much as 2 volts. The voltage response develops fully in the 100 microseconds needed for the full thickness of the film to be heated or cooled, and the signal is quite linear for small temperature changes. Applying a PVDF film to a thin polyester film on which the tissue was placed and leading the PVDF electrical response into the summing point of an operational amplifier, they were able to make a device that could detect 10 microdegree changes in 10 milligram tissue samples in 10 milliseconds. The device was so much more sensitive than thermopiles that signal averaging was usually not needed. Despite its great advantages, Tasaki's and Iwasa's PVDF device was limited in several ways.

(1) It was assembled by bonding together polyester, platinum, and PVDF layers with epoxy resins. Their high viscosity makes it difficult to achieve very thin bonding layers and only one or two devices can be made at a time because of the long setting time of the resin. Also, the detectors are too thick, making their unloaded heat capacity too great and their response times too long.

(2) The pyroelectric charge displacement from the PVDF was converted to a voltage signal by an operational amplifier with a junction field-effect transistor input whose feedback element is a resistor of about 10 gigohms. Because the amplifier must work at high impedance levels and because such large resistors have 1–2 picofarads of shunt capacitance, the high-frequency response of the system is limited. Moreover, the thermal noise generated in the feedback resistor contributes appreciably to the system noise. The resistance of such large resistors is moisture-sensitive and they are usually enclosed in bulky sealed glass tubes to improve their stability.

DISCLOSURE OF THE INVENTION

The present invention was designed to overcome many of the disadvantages associated with prior art detector assemblies.

Accordingly, the present invention provides a detector assembly having electrical- and thermo-responses that are easily reproducible, which can be produced economically in sufficient quantities for commercial applications. In this regard, the detectors of the present invention are assembled by use of a low-viscosity cyanoacrylate adhesive, which bonds in seconds to layers less than 0.5 millimeters thick.

The present invention further provides an amplifying system for use in connection with the detectors which produces signal band widths that exploit the full frequency range of the detector elements. In this regard, the amplifying system of the present invention utilizes low-loss capacitors as feedback elements whose behavior is much closer to that of ideal circuit elements having no dissipation and thus no thermal noise. Additionally, the amplifying system of the present invention utilizes preamplifiers that operate at much lower impedance levels than prior detector systems, thus yielding signal band widths that exploit the full frequency range of the detector elements.

In addition to the above, the amplifying system provided for in the present invention is capable of handling even fast temperature changes that are less than 100 millidegrees K. in size. In this regard, the amplifying system according to the present invention utilizes preamplifiers that integrate pyroelectric currents which are generated from the detector whose preamplifiers will not overload the input stages even at the fast anticipated temperature changes.

Also provided by the present invention is an electrical circuit that includes an automatic reset means which operates on feedback capacitors to thereby generate reset signals which can be counted electrically to follow large temperature excursions.

Together with the above, the present invention further provides for means to support and tension the detector element whereby mechanical background signals can be eliminated.

Other objects and advantages of the present invention will become apparent as the description thereof proceeds.

The pyroelectric detector of the present invention includes a supported pyroelectric film in which a voltage or current is produced as a result of heat conduction from a sample placed on the film.

There is also provided by the present invention a pyroelectric calorimeter which includes means for supporting the detector assembly and electrical circuitry means for receiving a signal generated by the detector and for producing therefrom a useful output signal. The support means of the present invention is particular in that means are provided in the support for properly tensioning the detector film.

There is further provided by the present invention a method for determining the heat capacity and heat conductivity of small liquid or solid samples.

With these and other objects in view, the present invention will be better understood from the description and the claims which follow hereinafter taken with reference to the drawings.

A more complete appreciation of the invention and many of the attendant advantages thereof will be readily perceived as the same becomes better understood by reference to the following detailed description when considered in connection with the accompanying figures.

BRIEF DESCRIPTION OF DRAWINGS

The present invention will now be described with reference to the annexed drawings, which are given by way of non-limiting examples only in which.

Other objects, advantages and features of the present invention will become apparent to those skilled in the art from the following discussion.

BEST MODE FOR CARRYING OUT THE INVENTION

Figure 1:
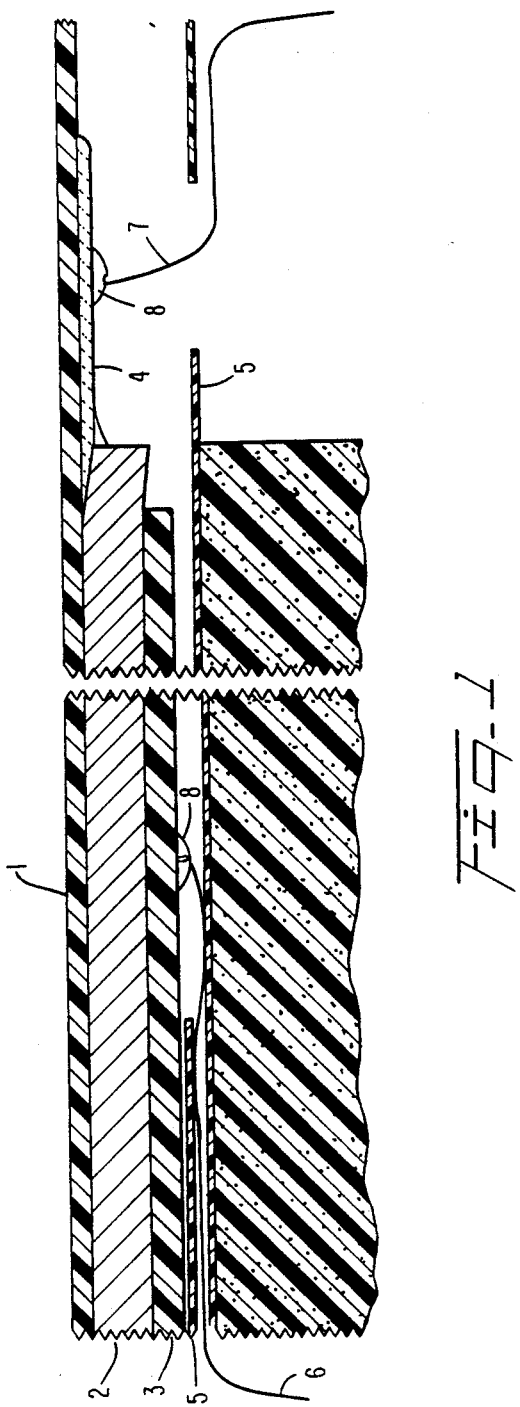
FIG. 1 is a cross-sectional view of the detector assembly according to the present invention.

As illustrated in FIG. 1, the detector assembly of the present invention includes polyester film 1 (mylar) which is cemented to a circular disk of aluminum foil 2. The polyester film has a thickness between about 2.0–6.0 $\mu$m. The circular disk of aluminum foil has a diameter of about 6.3 mm and a thickness of about 18 $\mu$m.

In attaching the polyester film to the circular disk of aluminum foil, it is important that the film be tightly stretched. Therefore, prior to attaching the aluminum foil, the polyester film is tightly stretched across the end of an open ring of a stretcher assembly. Next the aluminum foil disk is cemented to the center of the film with about a 0.3 $\mu$l drop of 3M cyanoacrylate adhesive type CA-40. The layers are compressed between two flat polytetrafluoroethylene coated bars held in an arbor press under about 10 kg/cm$^2$ pressure for about 30 seconds. After the adhesive has cured, the polyester film is cut free from the stretcher assembly.

As illustrated in FIG. 1, a circular piece of pulled metal-coated poly(vinylidene 1,1-difluoride) (KYNAR ®, Pennwalt Corporation, King of Persia, Pa.) 3 is cemented to the aluminum foil, on a side opposite to that of the polyester film. The poly(vinylidene 1,1-difluoride) has a diameter of about 6.5 mm and a thickness of about 8–9 $\mu$m and is cemented to the aluminum foil with about 0.3 $\mu$l of CA-40 adhesive under pressure.

An electrical contact is provided for the upper surface of the poly(vinylidene 1,1-difluoride), by applying a thin strip of silver paint 4, drawn radially outward from the aluminum foil onto the polyester film and allowed to dry. The width of the strip of silver paint is about 1.0 cm.

To the bottom of the poly(vinylidene 1,1-difluoride) is cemented at least one insulating polyester film 5 having through holes aligned with the center of the PVDF film and with the strip of silver paint so that electrical leads 6 and 7 passing through the holes could be in contact with the lower surface of the PVDF film and with the strip of silver paint. In a preferred embodiment a single polyester film of about 2.0 $\mu$m thick is stretched in a suitable stretching apparatus and 2 mm holes are formed in the polyester film about 1.0 cm apart by contact with the tip of a small, hot soldering iron. The insulating polyester film is cemented to the detector assembly with a ring of cyanoacrylate adhesive near the outer circumference thereof.

The two electrical leads 6 and 7 are connected to a lower center of the PVDF film and to the strip of silver paint. Preferably, the electrical leads are made of strands of graphite yarn about 3.0 cm long containing 5–10, 6 micrometer diameter fibers and are cemented to the detector with about 0.1–0.2 microliter drops of conductive carbon paint 8. The two leads are in contact with two sides of the PVDF film, the one, 6, on the lower center of the film being in direct contact and the other lead, 7, being in electrical contact through the aluminum disk which is tightly pressed against the metal coating of the PVDF film which comprises either a nickel or an aluminum coating.

The film elements of the detector assembly are supported by a circular polycarbonate disk 9 which has a diameter of about 3.2 cm and which is about 3 mm thick. The film elements extend across a tapered hole in the center of the polycarbonate disk which is about 1.0 cm in diameter. The film elements and the polycarbonate disk make up the detector of the present invention.

Figure 2:
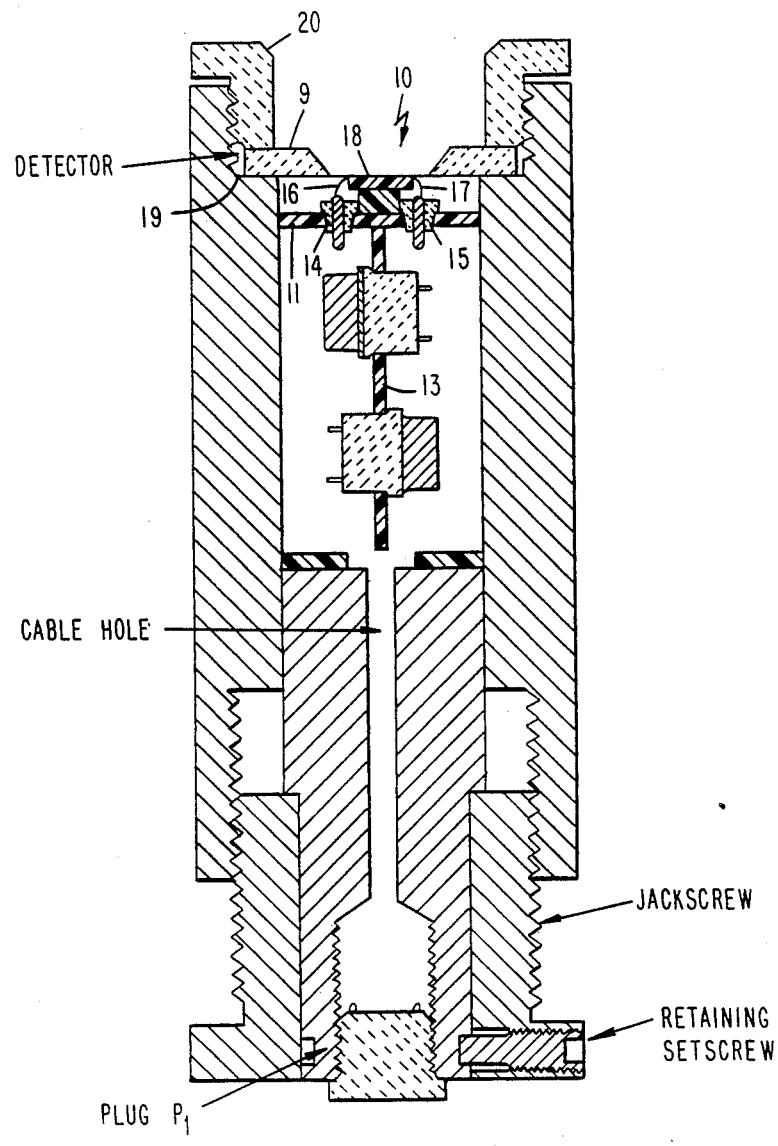
FIG. 2 is a cross-sectional view of the pyroelectric calorimeter of the present invention.
Figure 3:
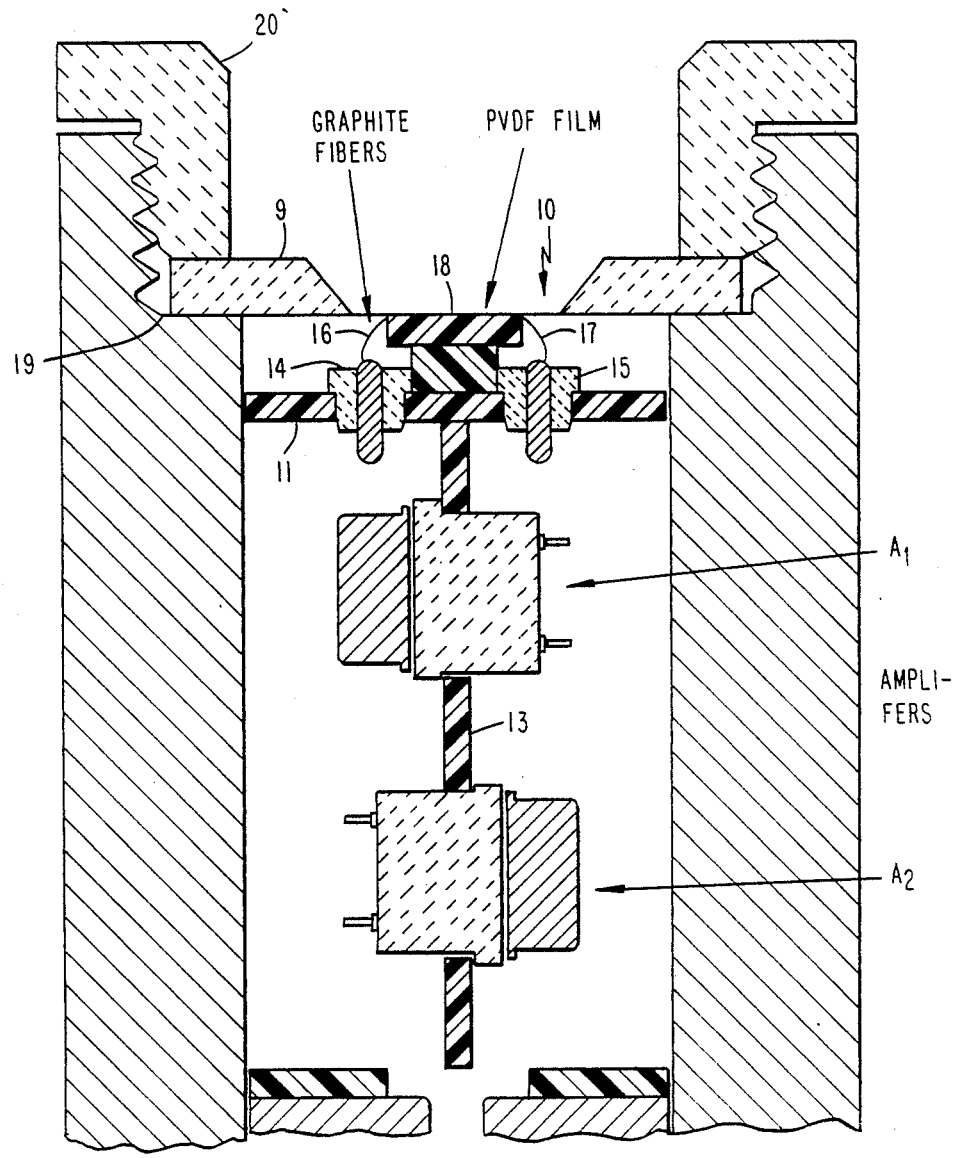
FIG. 3 is a detailed view of the pyroelectric calorimeter illustrated in FIG. 2.
Figure 4:
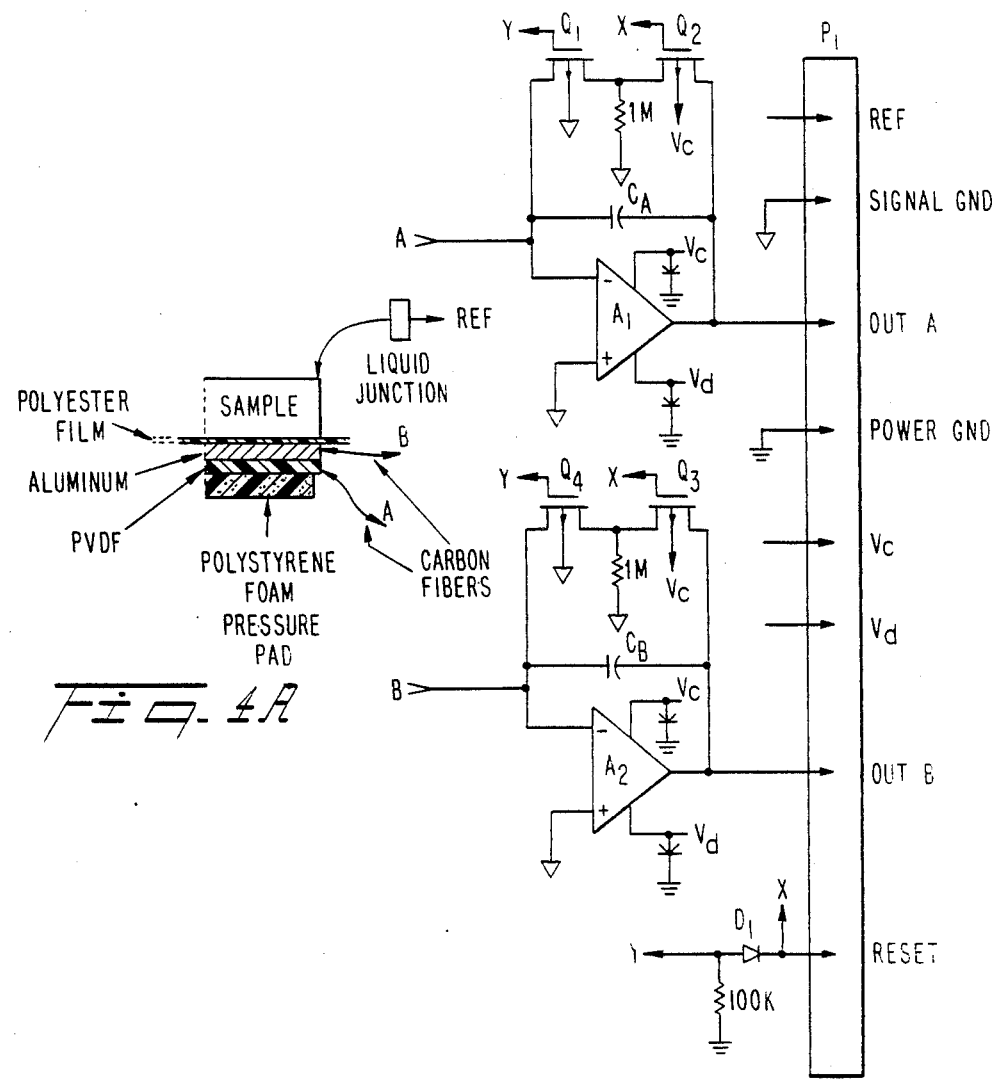
FIG. 4 is a diagram illustrating the preamplifier circuit used in connection with the pyroelectric calorimeter of the present invention.

A well 10 about 2.0 mm in diameter and about 2 mm deep is defined by the tapered hole in the center of the polycarbonate disk as illustrated in FIGS. 2 and 3. A fine silver wire is brought into the well through a hole in its bottom. The wire is cemented in place with an epoxy resin to form a water-tight seal. A portion of the wire located in the well is chlorinated to form a reversible electrode. Part of the wire extending through the polycarbonate disk is attached to a graphite lead and serves as a reference electrode (FIG. 4).

It has been found that detectors made as above, using a 6.3 micrometer thick polyester film from the aluminum disk support, have a typical capacitance of about 380 pF in series with 400$\Omega$. The capacitance between the aluminum disk and an electrolyte solution above the polyester film is about 75 pF.

FIGS. 2 and 3 show a cross-sectional view of the pyroelectric calorimeter of the present invention. A spool-shaped preamplifier is mounted on a cylindrical aluminum bar with one end facing upward toward the detector assembly. The preamplifier is made by cementing two copper-clad epoxy-fiberglass disks 11 and 12 to a rectangular epoxy-fiberglass piece 13 on which the circuit components are mounted as shown. The disk facing the detector 11 has polytetrafluoroethylene-insulated feedthroughs 14 and 15 to which the two graphite fiber leads 16 and 17 are attached with carbon paint.

Graphite yarn with individual strands of diameter of about less than three microns may be utilized to connect to the polyvinylidine difluoride detector and the insulated feed throughs 14 and 15 described above. This material is preferred because it is commercially available as an inexpensive, easily subdividable bundle of extremely flexible fibers which exhibits good electrical conductivity although preserving a low thermal conductivity.

To facilitate the attachment of the leads, the amplifier is raised with a jack-screw located at the lower end of the housing assembly as illustrated in FIG. 2 until the amplifier protrudes from the aluminum housing. The detector is then carefully rested on a styrofoam pad 18 which is attached to an upper portion of the spool and the entire assembly is then lowered until the detector's polycarbonate disk contacts a ledge 19 formed in the upper portion of the outer housing. A Delrin retaining ring 20 is then screwed in to hold the detector secure. The aluminum bar is then carefully raised with the jack-screw until the polystyrene foam pressure pad presses gently against the detector and dampens out any vibrations. The jack screw assembly makes it possible to control the tension on the detector and to adjust the tension so as to minimize mechanical sound pickup.

The space above the detector forms a water-tight and electrically insulated well into which solid and liquid samples can be placed. An aluminum cap closes the top of the well and excludes radiative and conductive heat paths. When needed, light flashes are delivered to the sample on the detector by a fiber-optic light pipe whose end is focused on the detector by a lens installed in the cap (not shown).

The preamplifier circuit as shown in FIG. 4 consists of two FET-input operational amplifiers $A_1$ and $A_2$, Burr-Brown type OPA111BM, in current-to-voltage mode. The feedback elements, $C_A$ and $C_B$ are polystyrene capacitors chosen to have leakage resistances $>10^{13} \Omega$. Because no dissipative elements are used in the feedback network, there is no thermal noise contributed by it. In addition, the capacitors are small, cheap and stable elements easily built into a compact preamplifier instead of costly, bulky high-megohm resistors.

The input current of each amplifier, typically 0.5 pA, causes each output to drift slowly and steadily. When either output reaches 0.8 volt, a reset circuit (FIGS. 5 and 6) turns on the switches composed of $Q_1 \theta Q_4$ for 1 millisecond to discharge the feedback capacitors. When open, the two switches have leakage conductances less than 10 picoSiemens and no detectable leakage current, because all elements of $Q_1$ and $Q_4$ are near ground potential.

Low-noise amplifiers $A_3$ and $A_5$ provide 10-fold d.c. gain from the two preamplifiers to drive the comparator reset circuit (FIG. 6), the differentiator, amplifiers $A_4$ and $A_6$ (FIG. 5), and direct outputs $V_A$ and $V_{AB}$. The preamplifiers and $A_3$ and $A_5$ are operated from $\pm 10$ volt supplies to decouple them from the later amplifiers.

The pyroelectric current generated by the PVDF element traverses $C_A$ and $C_B$ in opposite directions, so that a sum of the outputs of $A_1$ and $A_2$, $V_{ab}$, formed in $A_5$ is adjusted to be independent of temperature by varying $R_{32}$. But $V_{AB}$ is still responsive to capacitatively coupled potential changes between the reference junction and the sample on the polyester film just above the Al foil while $V_4$ is proportional to temperature change in the PVDF film.

$V_A$ and $V_{AB}$ are measured directly in calibrating the temperature and sample voltage responses of the detector. In addition, the two outputs are differentiated by amplifiers $A_4$ and $A_6$ to yield the amplified rates of change, $V_A$ and $V_{AB}$ in temperature and voltage.

Figure 5:
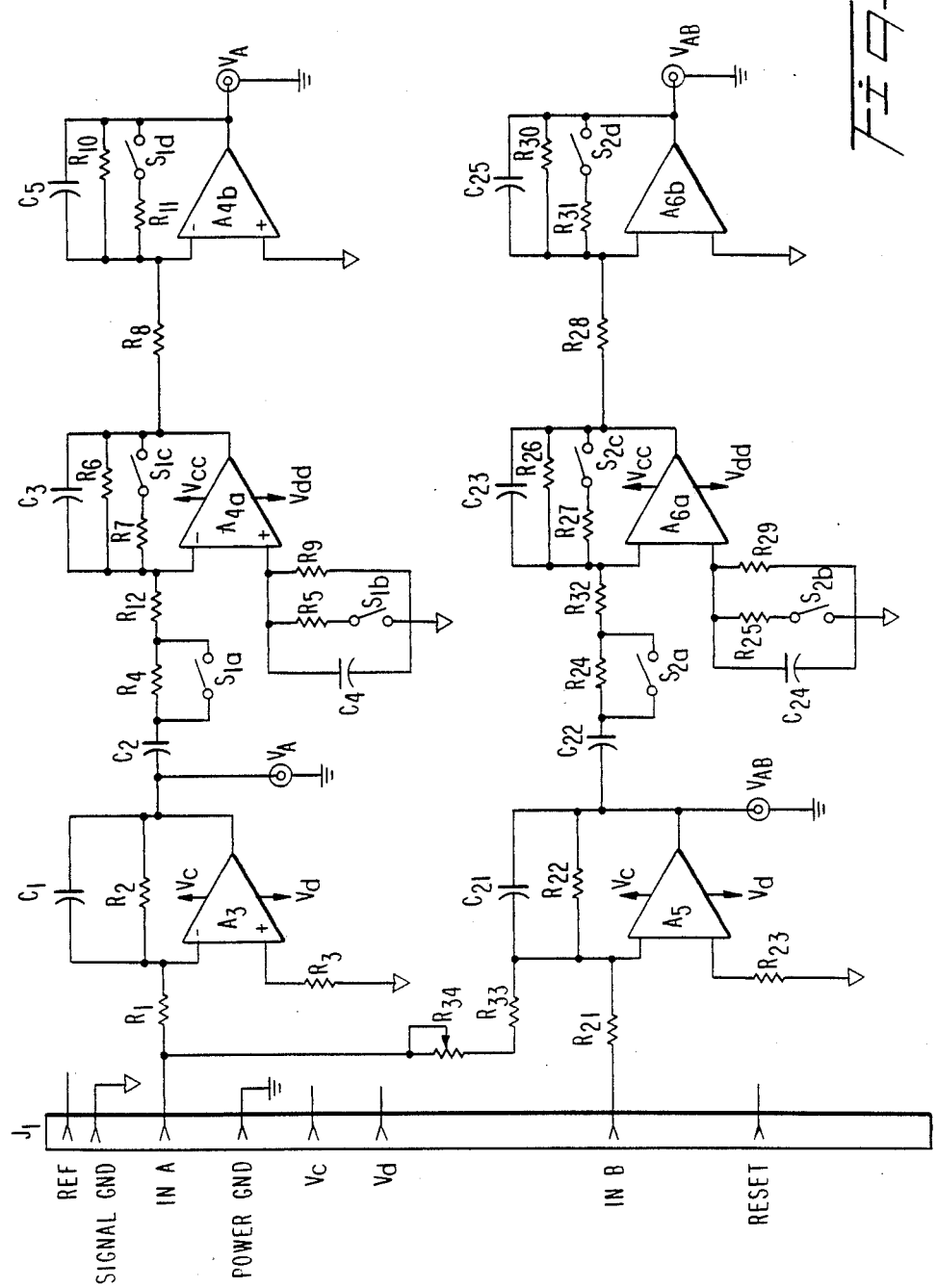
FIG. 5 is a diagram of the amplifier circuit used in connection with the pyroelectric calorimeter of the present invention.

In the circuit shown in FIGS. 4 and 5, $V_A$ is related to the pyroelectric current $I_p$ from the PVDF film by the equation $$V_A = I_p G_3 G_{4b} \frac{C_2}{C_A} \frac{R_6}{(1 + sC_2(R_4 + R_{12}))(1 + sC_3 R_6)} \quad (1)$$

in which $s = j2\pi f$, f is frequency in Hz and switches $S_1$ are open. $G_3$ and $G_{4b}$ are the closed-loop gains of amplifiers $A_3$ and $A_{4b}$. An identical relation applies for $V_{AB}$. In effect, the circuits are current-to-voltage converters with equivalent resistances of 309 G$\Omega$ with $S_1$ and $S_2$ open and 30.2 G$\Omega$ with the switches closed. The maximum gains of the differentiators occur at frequencies of 160 and 525 Hz, respectively, with the switches open and closed. When $S_1$ and $S_2$ are closed, trading gain for band width, the differentiators can follow submillisecond transients from the two channels of the detector. The temperature and voltage changes sensed by the detector are recovered by recording $V_A$ and $V_{AB}$ digitally and integrating the values numerically.

The PVDF detectors, calibrated with 10 nmK temperature steps in a Cu bar pressed against the polyester films, showed responses at $V_A$ of $4.0 \pm 0.3$ volt K$^{-1}$. With the PVDF film replaced by a 480 pF fixed capacitor, the equivalent input noise current of channel A of the amplifier from 0.1 to 20 Hz was 4.3 fA r.m.s., a figure equivalent to a thermal noise conductance of 58 pS. With the PVDF film connected and a 10 mg. sample of heat capacity 10 mcal K$^{-1}$ lying on the detector, the noise current increased to 8.5 fA, mainly due to pickup of mechanical vibrations from the ambient. After 1 sec. of integration, the noise current produced a system output with a standard deviation equivalent to 0.95 $\mu$V uncertainty in the potential across the sample after 1 sec of integration if the polyester film capacitance was 75 pF.

The heat capacity of a typical bare detector when mounted and connected in the holder with the polystyrene pressure pad in place is 1.8 millicalorie K$^{-1}$ when calibrated with 640 nm. light flashes of known absorbed energy.

The electronic circuits are enclosed in a cast aluminum box with tightly fitting covers that eliminate internal temperature gradients and exclude radio-frequency interference from broadcasting stations. The power input to the amplifier box and all signal outputs are passed through ferrite bead inductors to eliminate external electrical interference.

Figure 6:
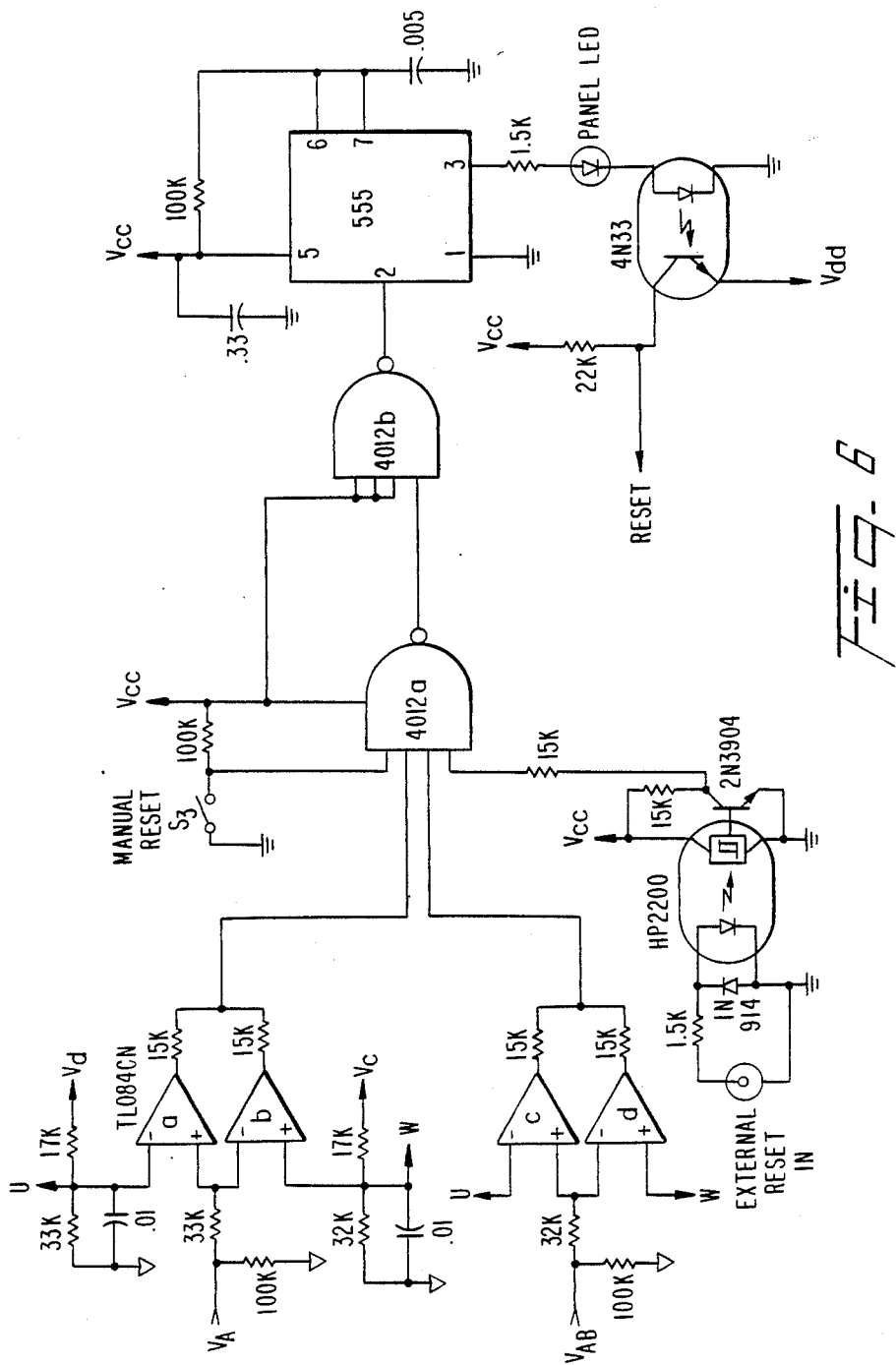
FIG. 6 is a diagram illustrating the comparator circuit used in connection with the pyroelectric calorimeter of the present invention.
Figure 6A:
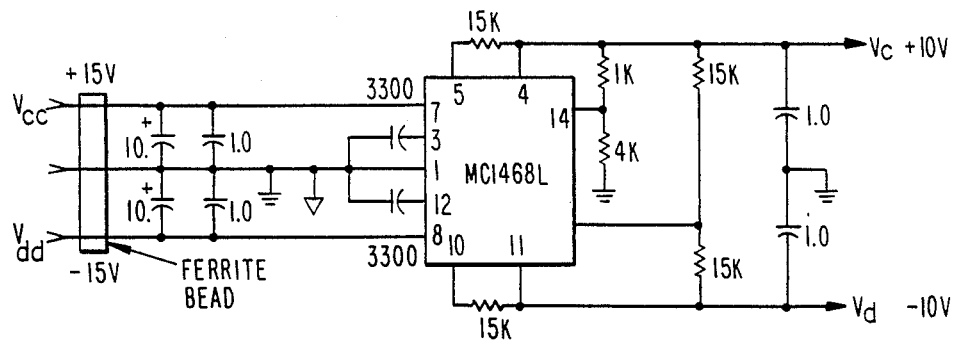

The circuits in FIGS. 4, 5 and 6 are built on epoxy-fiberglass circuit boards. Each operational amplifier in FIGS. 4 and 5 has its power drawn from the comparator board (FIG. 6) by separate leads decoupled to ground by unmarked 0.1 $\mu$f ceramic capacitors shown at the amplifier sockets.

The preamplifier (FIG. 4) and the first-stage amplifiers $A_3$ and $A_5$ are operated from separately regulated ±10 V supplies $V_c$ and $V_d$ to isolate the input stages from feedback from the output stages.

The preamplifier board shown in FIG. 4 mounts amplifiers $A_1$ and $A_2$ in polytetrafluoroethylene sockets. The amplifier inputs are connected directly to the detector, the feedback capacitors $C_A$ and $C_B$ and switch transistors $Q_1$ and $Q_4$ without touching the circuit board so as to minimize electrical leakage to the negative summing points A and B.

Effective performance of the preamplifiers in detecting small thermal signs depends upon setting their voltage gains high enough so that the electrical noise generated in the detector and $A_1$ and $A_2$ are large compared to that produced in subsequent stages and minimizing the first-stage noise. There are two main sources of first-stage noise in the detector and preamplifier: (a) mechanical vibrations from the laboratory environment sensed by the pyroelectric detector because of its piezoelectric responsivity, and (b) electrical noise generated in the detector and the first-stage transistors of the amplifiers.

Sensitivity to mechanical vibrations is minimized by pressing a cushioned polystyrene foam pad against the detector. The pressure of the pad is adjusted by the jackscrew device shown so as to give minimum detector sensitivity to sound and vibration.

The electrical noise power density spectrum of the detector-preamplifier system can be represented as the sum $I^2_n(f)$ of four statistically independent fluctuating input currents introduced at the negative input of each preamplifier. These are:

(i) a thermal noise current of power density $\overline{i^2_{th}}(f)$ at frequency (f) generated by the dissipative component $1/R_f$ of the total electrical admittance between the amplifier input and its output, ground, or other points with low impedances to ground (such as power supply leads), (ii) a thermal noise current $\overline{i^2_d}(f)$ due to voltage fluctuations $\overline{e^2_d}(f)$ in $R_d$, the sum of the electrical resistance of the carbon fibers attaching the detector to the preamplifier and the dielectric loss resistance of the PVDF film and its conductive metal coatings, (iii) fluctuations $\overline{i^2_b}(f)$ in the preamplifier input bias current, and (iv) random currents $\overline{i^2_e}(f)$ caused by fluctuations $e^2_n(f)$ in the offset voltage of the input stage of the amplifier. These noise sources are shown schematically in FIG. 7.

Because the four noise currents are statistically independent, $$\overline{I^2_n}(f) = \overline{i^2_{th}}(f) + \overline{i^2_d}(f) + \overline{i^2_b}(f) + \overline{i^2_e}(f). \quad (3)$$

Nyquist's theorem then predicts that $$\overline{i^2_{th}}(f) = 4kT/(R_f(1+\omega^2\pi_f^2)) \quad (4)$$

in which k is Boltzmann's constant, T is absolute temperature, $\omega = 2\pi f$ and $\pi_f = R_f C_f$. Similarly, $$\overline{i^2_d}(f) = 4kTR_d\omega^2C^2_i/(1+\omega^2\pi^2_i), \quad (5)$$

similarly where $\pi_i = R_d C_i$. The noise currents due to the amplifier input stage are:

$$i^2_b(f) = i^2_n(f)(1+\omega\pi^2_f) \quad (6)$$

and $$\overline{i^2_e}(f) = \overline{e^2_n}(f)\omega^2 C^2_i/(1+\omega\pi^2_f), \quad (7)$$

in which $i^2_n(f)$ and $e^2_n(f)$ are obtained from empirical measurements on the preamplifiers at various frequencies (f).

Figure 7:
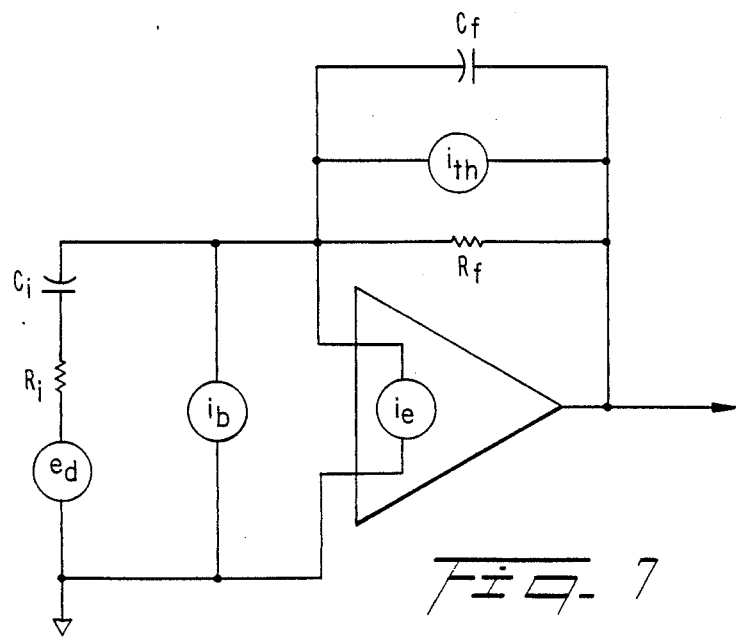
FIG. 7 is a diagram illustrating an amplifier detector arrangement.

Equations 4–7 apply for any amplifier-detector arrangement shown in FIG. 7. However, if the main conductance $1/R_f$ across the capacitor $C_f$ is eliminated as in the design shown in FIG. 4, the noise current $\overline{i^2_{th}}(f)$ is eliminated, while $$\overline{i^2_b}(f) = \overline{i^2_n}(f) \quad (6')$$

and $$\overline{i^2_e}(f) = \omega^2 C^2_i \overline{e^2_n}(f) \quad (7')$$

Table I shows values for the noise components of equation (3) in the preamplifier taken from data sheets supplied by Burr-Brown for type OPA111IBM operational amplifiers and by Pennwalt for PVDF film.

TABLE I

Noise current sources in pyroelectric detector-amplifier of FIG. 7.

| Frequency Hz | $i_e$ | $i_b$ | $i_d$ | $I_n$ |
|---|---|---|---|---|
| 1.0 | 0.065 | 0.40 | 0.003 | 0.4 |
| 1 | 0.22 | 0.40 | 0.027 | 0.45 |
| 10 | 0.72 | 0.40 | 0.27 | 0.86 |
| 100 | 2.6 | 0.40 | 2.7 | 3.8 |
| 1000 | 17. | 0.40 | 27. | 32. |
| $10^4$ | 140. | 0.50 | 250. | 290. |

Noise current spectral density of a 10 GΩ resistor is 1.26 fA/(Hz)$^{\frac{1}{2}}$. Based on data for Burr-Brown type OPA111IBM operational amplifiers in data sheets of the manufacturer, dielectric loss specifications for PVDF "Kynar" film as supplied by Pennwalt Corporation and equations (3–7). Noise current spectral densities in units of femtoamperes/(Hz)$^{\frac{1}{2}}$.

The total input current noise density $I_n$ shown in Table I is equivalent to the thermal noise generated in a 80 GΩ resistor across $C_f$. If the feedback circuit in the preamplifier were to use such a large resistor instead of $C_f$, the circuit would have a poor high frequency response and would be only marginally stable because of the high electrical capacity of the PVDF film. If a lower value of feedback resistance were used, its noise would degrade the system noise figure and thus its sensitivity to small temperature changes.

Practical realization of the low-noise preamplifiers of FIG. 4 requires that the feedback capacitors $C_A$ and $C_B$ have the lowest possible electrical leakage. Polystyrene capacitors with insulation resistance exceeding $10^{13}\Omega$ are used so that the transfer characteristic of each amplifier is that of an ideal integrator. The transistor switches $Q_{1-4}$ were also chosen to have the lowest leakage possible in commercially available MOSFET devices. When in the open state, their leakage conductance to the preamplifier inputs are less than 5 picoSiemens.

Since the preamplifiers acted as integrators whose outputs slowly drift in response to the input bias currents of $A_1$ and $A_2$, the drift must be compensated and the charge accumulated in $C_A$ and $C_B$ removed from time to time. This is accomplished by first amplifying the preamplifier outputs tenfold in amplifiers $A_3$ and $A_5$. Their two outputs are fed to comparators shown in FIG. 4, which generate 1 millisecond reset pulses that close the MOSFET switches across $C_A$ and $C_B$ whenever the output level of either $A_3$ or $A_5$ exceeds ±8 volts. In order that no additional noise be introduced by $A_3$ and $A_5$, type OP27A operational amplifiers are used. These have relatively large input bias currents but extremely low voltage noise $e_n$. When driven by the low output impedances of the preamplifiers through coupling resistances $R_1$, $R_{34}+R_{33}$ and feedback resistances $R_2$ and $R_{22}$, $A_3$ and $A_5$ yield essentially noiseless gains of 10. To assure that the coupling resistors introduce no significant thermal noise, $R_1$ and $R_{34}+R_{33}$ are 2000 ohm metal film resistors or potentiometers. The outputs of the two amplifiers are available at $V_A$ and $V_{AB}$ for purposes of calibrating the detector.

$V_A$ and $V_{AB}$ are differentiated by amplifiers $A_{4a}$ and $A_{6a}$ through 0.068 $\mu$F polyester coupling capacitors $C_2$ and $C_{22}$. $C_3$ and $C_{23}$ together with $R_4+R_{12}$ and $R_{24}+R_{32}$ attenuate the high-frequency responses of the differentiators above 1 kHz, the corner frequencies being switchable via MOSFET switch banks $S_1$ and $S_2$, Analog Devices type AD7510. Amplifiers $A_{4b}$ and $A_{6b}$ provide additional adjustable gain and low output impedances to drive long cables to recording devices. In the arrangement shown in FIG. 5, the transistor switches reduce the system gain tenfold and raise the corner frequency 3.2-fold when closed. $A_4$ and $A_6$ are Analog Devices type AD647K dual JFET operational amplifiers. 1% precision metal film or carbon film resistors are used throughout. With $S_1$ switches open, the preamplifier-amplifier combination gives an output response equivalent to that which would be obtained in the pyroelectric current from the detector were passed through a current-to-voltage converter of effective resistance $3.1 \times 10^{11} \Omega$. With $S_1$ closed, the effective resistance is tenfold less. Table II gives values of the components used in FIG. 5.

TABLE II

Components used in the circuits of FIG. 5.
All resistors ¼ watt. m.f.: metal film; c.f.: carbon film.

| Resistors | | Capacitors | |
|---|---|---|---|
| | 2.0K m.f. | 1,21 | 270 pF |
| 2 | 20K m.f. | 2,22 | 0.068 $\mu$F 100 w.v. Mylar |
| 3 | 1.8K m.f. | 3,23 | 100 pF |
| 4,24 | 10K m.f. | 4,24 | 0.01 $\mu$F 50 w.v. Cerami |
| 5,25 | 4.4 M c.f. | 5,25 | 1000 pF 50 w.v. ceramic |
| 6,26 | 10 M c.f. | | |
| 7,27 | 4.7 M c.f. | Semiconductors | |
| 8,28 | 10K m.f. | $A_3$, $A_5$ | OP27A Op. Amp. |
| 9,29 | 10 M c.f. | $A_4$, $A_6$ | AD647K Dual Op. Amp. |
| 10 | 100K m.f. | $S_1$, $S_2$ | AD7510 Switches |
| 11 | 47K m.f. | | |
| 12,32 | 4.7K m.f. | | |
| 21 | 5K m.f. | | |
| 22 | 50 m.f. | | |
| 23 | 2K m.f. | | |
| 30 | 274K c.f. | | |
| 31 | 130K c.f. | | |
| 33 | 4.5K m.f. | | |
| 34 | 2K cermet adj. | | |

In order to determine the heat capacity and heat conductivity of small thin samples of liquids and solids, the sample is laid on the upper surface of the detector so as to form a layer of uniform thickness in intimate contact with the polyester layer. A microsecond-duration light flash of known energy is delivered to the sample. If the wavelength of the light is such that no light is absorbed in the sample itself, the light absorbed in the Al foil of the detector causes a temperature jump $q_d$, of characteristic shape whose amplitude at times less than 1 millisecond is proportional to absorbed light energy. The heat then flows up through the sample and the detector temperature falls rapidly along a curve characteristic of the sample's thermometric conductivity to a final level inversely proportional to the sample's total heat capacity. From this level, the sample cools to the ambient with a time constant that is usually much longer than the spreading time of heat within the sample itself.

Alternatively, a 2 $\mu$m thick light-absorbing film of polyester coated by vacuum evaporation with nickel, bismuth or antimony or equivalent material can be laid on the sample and exposed to a microsecond light flash. The temperature rise observed by the detector is a unique and characteristic function of the thickness, thermometric conductivity, and heat capacity of the sample. The latter two quantities can be determined by curve fitting with solutions of the differential equation for heat conductivity if the sample weight and the absorbed light energy are known.

A light-absorbing sample on the detector affects the detector response to a microsecond light flash in two ways: First, it diminishes the amplitude of $q_d$ from that of the unshielded detector to a lesser value in proportion to fraction on incident light absorbed in the sample. Second, the sample is directly heated by the photons absorbed within it, causing a temperature change $q_p$, to appear at the pyroelectric PVDF element. Since an overlying polyester film has a much lower heat conductivity than the Al foil, $q_p$ is much slower than $q_d$ and can be resolved from it by curve stripping. The exact time course depends upon the spatial distribution of the absorbed light in the sample and upon its heat conductivity and thickness. The size of $q_p$'s contribution to the final temperature rise caused by a flash divided by the reduction in $q_d$'s contribution to measures the efficiency of conversion of light energy to heat. If the sample contains a fluorescent layer, for example, the energy carried away as re-emitted fluorescence will reduce the heating effect of the absorbed light energy.

In addition to measuring the heat capacity and heat conductivity of samples, the detector of the present invention has been particularly developed to measure light-induced metabolic events in living cells and tissues. In this regard, the great sensitivity of the detector permits the measurement of micromolar changes in the levels of high energy phosphate esters in tissue samples of retinas, for example, when stimulated by as few as 100 absorbed photons per photoreceptor cell.

A vertebrate retinal rod responds to photons absorbed in its outer segment (OS) disk membranes by briefly reducing the dark current flowing through the overlying plasma membrane, hyperpolarizing the cell. Since OS contains a light-activated cGMP phosphodiesterase (PDEase) and the cationic conductance of outer segment membranes increases rapidly and reversibly on exposure to $>5$ $\mu$M concentrations of cGMP, transduction based on control of the dark current conductance by free cytoplasmic cGMP has been proposed.

The following example compares the heat produced by frog retinas during transduction with that generated when cGMP is split by PDEase. Although cGMP yields 11 kcal/mol of heat on hydrolysis to 5'-GMP, the tiny amounts believed split during light responses would yield heats measurable only by radically improved calorimetry. The present method, based on heat detection by pyroelectric polyvinylidene (1,1-difluoride) (PVDF) films, extends the range of chemical calorimetry to submicrodegree levels and millisecond times.

Having now generally described this invention, the same will be better understood by reference to certain specific examples, which are included herein for purposes of illustration only and are not intended to be limiting of the invention or any embodiment thereof, unless so specified.

EXAMPLE

Dark-adapted bullfrog (*R. catesbiana*) retinas, removed under infrared illumination, were stored for 10 min to 1 hr in an oxygenated bath containing (in mM) Na+:100, K+:2.7, Ca++:1.4, Mg++:0.5, phosphate:0.5, HEPES:10, glucose:11, EDTA:0.01, pH 7.1. Cl− was the main anion. Disks 6.3 mm. across were cut from a retina and attached by their vitreal surfaces to 25 $\mu$m. thick nylon mesh (Small Parts, Ltd., Miami, Fla.) disks of the same diameter.

Before use, each disk was soaked for 5 min in a medium containing 10 mM glutamate and 5 mM cysteine to suppress electrical responses from all retinal cells except the rods, cones and glial Muller cells. Using an infrared viewer, the disks were placed on the detector with receptor layer down and excess fluid was blotted away. Flowing moist oxygen replaced the atmosphere every 2 m.

6 $\mu$s flashes of spectral width 70 nm. centered at 500, 550 or 640 nm. from a Xenon flash tube were attenuated by a circular graded wedge and fed via a light pipe whose end was projected to a 6 mm circle at the retina. A computerized stepping motor turned the wedge so that flashes of varying intensity could be quickly delivered. The light input at the retina was measured with a silicon photovoltaic diode (International Light, Inc., Newburyport, Mass.). Exposures of the OS were calculated for a rod density in the retinal mosaic of $1.76 \times 10^6$ cm$^{-2}$. Cone and green rod pigments were neglected and rod porphyropsin was lumped with rhodopsin. Assuming the quantum efficiency of rhodopsin photoisomerization to be 0.6 and its molar absorbance at 550 nm to be $2.0 \times 10^4 M^{-1} cm^{-1}$, its isomerization cross section $Z_R$ was $4.6 \times 10^{-17}$ cm$^2$.

The weight fraction of rod outer segment cytoplasm in retinas was estimated to be 7% from (a) the measured OS lengths (50±5 $\mu$m in 4 retinas), (b) the fraction of the retinal mosaic area composed of OS cross-sections (50% in 2 measurements) and (c) the water fraction in the OS mass (0.7±0.05).

The enthalpy of hydrolysis of cGMP to 5'-GMP by rod PDEase was measured by mixing two parts of a suspension of totally bleached frog rod outer segment membranes harvested from a continuous Metrizamide density gradient (D-1.01–1.11) with one part of 300 $\mu$M cGMP in a cytoRinger containing (in mM) K+:80, Na+:40, Cl−:80, HOEtSO3−:40, MOPS:10(pH 7.15), MgSO4:5, CaCl2:0.1, EDTA:0.02. The rhodopsin concentration in suspension before bleaching was 12 $\mu$m. Heat evolution was measured in an LKB batch calorimeter 15 25° C. $\Delta$H observed was 11.2±0.7 (n=2) kcal mol$^{-1}$ cGMP hydrolyzed.

When a light flash falls on a detector bearing a retinal disk whose rods have been light adapted by bleaching 1% of their rhodopsin, the detector's thermal response shows two components, $q_d$ and $q_p$, with different time courses. For flashes $<10^8$ incident photons rod$^{-1}$ both are proportional to flash energy. $q_d$ is due to light reaching the A1 layer, where 18±2% is absorbed, converted to heat and spread through the full thickness of the PVDF film within 100 $\mu$s. The slower $q_p$ is due to photons absorbed in the OS. Since the polyester film has a heat conductivity 1000-fold less than A1, the first 800 $\mu$s of the detector response is entirely from $q_d$ and can be used to remove its contribution to the composite responses by curve stripping. $q_p$ then gives the detector response to a sudden heat burst released in the OS. $q_d$ and $q_p$ show large initial overshoots because the sources are close to the PVDF film. As the heat then spreads up through the retina in a time $T_S$ of 20–30 ms., the PVDF temperature drops to a plateau, then declines to the ambient with a Newton's law time constant $T_N$ of about 2 m. $T_N$ is much shorter for the bare detector whose heat capacity was equivalent to 1.8 mg of water.

For times $<<T_N$ and $>>T_S$ the specimen is almost isothermal and adiabatic, so using 650 nm flashes of known energy that heated only the A1 layer, the specific heat, $C_p$, of the sample was estimated from the temperature rise at 2.5 s. $C_p$ for the 13.6 mg. specimen was 0.86±0.04 (n=4). The relative sizes of $q_d$ at 640, 500, and 550 nm. produced by equal energy incident flashes express the retina's light transmission. Assuming no OS absorption at 640 nm., the rods absorbed 0.59 and 0.50 photons at 500 and 550 nm., respectively, yielding 0.77±0.04 and 0.80±0.03 (n=2) of the photon energy as heat. These values are near those found by calorimetry on cattle rods.

Light flashes absorbed in the OS of dark-adapted retinas elicit or other heats besides $q_d$ and $q_p$. By using a rapid series of flashes of increasing energy these can be resolved into components of two types: heat bursts, q, that raise the sample temperature by microdegrees with apparently first-order kinetics and time constants of 100–300 ms., and slow heat fluxes, r, that cause steady increases (or decreases) in sample temperature for many seconds. Each component saturates in size at a exposure that bleaches far less than 1% of the rhodopsin.

These components are revealed in retinas exposed to eight 550 nm flashes ($F_1$ to $F_8$) at intervals of 5 and then 1.2 s. along with the transretinal (PIII) waveform. $V_r$ recorded together. Changes in transretinal voltage, the raw $\theta$ transients uncorrected for $q_p$ or $q_d$, and the temperature changed, obtained by integrating the raw $\theta$ transients numerically were observed. At Z, the integration restarted with the d.c. offset set to zero, to eliminate the downtrend in $\theta$ after $F_1$. $F_8$ produced $q_p+q_d$ alone. When the $F_8$ transient, scaled down to the incident flash energy of $F_{3-7}$ and shifted suitable in time, was subtracted from each transient before integration showed extra heat components besides $q_p+q_d$ was obtained. The heats following F3–F7 recovered in 20–40 s., but the small component seen at F1 and the Vr voltage waveform only recovered after dim flashes like F1 and F2.

In all, at least four new light-stimulated heat components: (a) a fast heat burst, $q_1$, during the quickly rising phase of $V_r$ warming the sample by 1–2 $\mu$K and completely evoked by $F_1$, (b) a steady cooling $r_1$, of about −5 $\mu$Ks$^{-1}$ persisting as long as the dark current is suppressed, (c) a slower heat burst, $q_3$, 20–50 $\mu$K in size rising in about 300 ms. after $F_{3-6}$ and (d) a steady warming, $r_3$, that increases after $F_6$ and $F_7$.

The heats produced by $F_{3-7}$ were replotted after correcting for $r_1$ and $q_p+q_d$, thus showing the incremental heat produced by each flash. Curve $F_3$ was fitted to the function $$H(t) = A(1 - e^{-Bt}) + Ct, \quad (8)$$

in which A, B, and C have been adjusted. A is the $q_3$ amplitude, B is its rate constant and C measures $r_3$. The summed amplitudes G of the Q3s were plotted against total exposure. The points from two samples are fitted to the equation $$G(E) = K(1 - e^{-E/E_0}), \quad (9)$$

where K is the total $q_3$ size and $E_0$ is the flash exposure yielding 0.632K. $E_0$ was 5.0 and $6.6 \times 10^{12}$ photons incident cm$^{-2}$ for the two retinas. Equation 9 portrays activation of a set of targets of cross section $1/E_0$, each releasing a fixed amount of heat when one or more PIs occurs within it.

In retinas incubated in glutamate Ringer containing 100 μV (100–1000 PI/OS) and a $q_1$ of 1–2 μK followed by steady cooling lasting for more than 20 s. or until the dark current resumed. A second flash while the dark current was suppressed (as judged by the absence of change in $V_r$) gave no $q_1$ and no change in $r_1$. In 30 experiments, $V_r$ responses, whose amplitudes corresponded to dark currents of 20–50 pA/rod, were accompanied by $q_1$ bursts of 0.8 to 2 μK (mean ±s.e.e.:1.09±0.05, n=24) while $r_1$ varied from −2 to −5 μKs$^{-1}$.

$q_1$ was unchanged by several agents that suppressed the dark current and changed $r_1$. In this regard, the effects of flashes causing 180 PI/rod on retinal temperature and transretinal voltage were studied with an average of 2–4 trials with 60 s intervals between flashes, during which $q_1$ recovered. 30 mM ca$^{++}$ in the incubation fluid reduced $V_r$ sixfold and changed $r_1$'s sign while $q_1$ remained 12.0±0.4 (n=4) μK. Retinas incubated in 50 μM ouabain for 10 m. showed no $V_r$ even though the cells retained 20 mM of cytoplasmic K$^+$ and produced light-sensitive dark current if the external [Ca$^{++}$] was suddenly lowered to 1 μM. Nevertheless, a 180 PI/OS flash produced a $q_1$ of 1.6±0.1 (n=3) μK and $r_1$ of 4 μK/s.

$q_1$ increased to 2.4±0.4 μK (n=3) when 20 mM imidazole, a permanent nontoxic pH buffer, was added to the incubation medium and became the main cytoplasmic buffer for protons produced during cGMP hydrolysis. Its 7 kcal mol$^{-1}$ ΔH of neutralization adds 3.5 kcal mol$^{-1}$ to the total heat from cGMP if normal cytoplasm is mainly buffered by phosphates.

500 μM IBMX suppressed both $V_r$ and $q_1$ at 180 PI/rod. Tenfold brighter flashes yielded slow $V_r$ waves and delayed $q_1$ heats of 2.1±0.1 (n=6) μK.

The kinetics of normal $q_1$ and $v_r$ were next compared. If $q_1$ is produced in the outer segment layer with the same spatial distribution as $q_p$, the θ curves can be corrected for the overshoot in the detector's $q_p$ response by deconvolution. This yields thermal traces that would have been observed if the $q_1$ heat had been uniformly released throughout the full thickness of the sample. At low exposures $q_1$ preceded $V_r$. At higher levels $q_1$ was unchanged but $V_r$ became faster, so that the two processes became almost simultaneous. $q_1$ was never slower than $V_r$ and always accompanied it.

The excitatory cascade suggested for phototransduction in rods consists of five coupled cycles: the rhodopsin cycle R, a G-protein cycle G, a PdEase cycle P, the cGMP cycle C, and the dark current cation cycle D. In darkness, the R, G, and P cycles are each poised with their levels of intermediates determined by pileup behind a single strongly inhibited bottleneck reaction. The C cycle is possibly not completely inhibited in the dark. A flash that activates a cycle will cause (a) a transient "activation heat" q as the levels of intermediates change from the dark values to those obtaining when the bottleneck reaction is turned on, and (b) a sustained "cycling heat" r as the intermediates pass through the cycle. r will die away as the bottleneck reaction slows, but in an efficient transduction mechanism the two heats should have widely different time courses. Both q and r can be composites of endo- and exothermic components. Partial activation of a cycle should produce smaller, slower q's and r's.

The activation flash energy relation for each cycle depends on its coupling to adjacent cycles and on the abundances of molecular types relative to rhodopsin. For the G and P cycles, in which one MetaII molecule, R* can activate $M_G$ G-proteins, each then activating one P and splitting a GTP, the activation cross-section $Z_p$ will be $Z_R \times M_R \times M_G \times N_R/N_P$. And the fraction F(E) of Ps activated by a flash of energy E will be of the form of eq. (9) in which $Z_p$ will be equivalent to $1/E_0$. Estimates predict a $Z_p$ of as much as $800,000 \times Z_R$ for the P cycle in amphibian OS. The above investigation shows cross-sections for $q_3$ of 5600 and 7500 times $Z_R$. If the total $q_3$s, 58 and 887 μK, arose from GTP hydrolysis in the G cycle yielding 4.8 kcal mol$^{-1}$, 220 and 330 μM GTP would be consumed in the OS of the two samples. The coupling gains $M_G$ are then 290 and 560 GTPs split per PI. Total GTP split by isolated frog OS 20 s. after bleaching 1% of their rhodopsin is larger, possibly because much is used in reactions producing $r_3$.

The cGMP control model and the responses of rod membrane patches to applied cGMP shape expected heat events during dark current shutdown. Membrane patch conductance $g_m$ depends on free [cGMP] c according to the relation $$g_m = g_{max} \frac{c^n}{c^n + K_c^n}, \quad (10)$$

where $g_{max}$ is the maximum cGMP-induced cationic conductance. n ranges from 2 to 3 and the dissociation constant $K_c$ is 10–42 μM in various studies. The cGMP control hypothesis then predicts:

(1) A full size $q_1$ should be produced by <1 PI per 10 OS disks.
(2) If the dark current is suppressed by light, more light should yield little more $q_1$ heat.
(3) The retinal heating due to cGMP hydrolysis during transduction will be >3.5 μK. This figure follows from eq. (10) if (a) the usual dark current conductance is 1/15 of $g_{max}$, (b) $K_c$ is 10 μM, (c) n=3, (d) the outer segment cytoplasm is 7% of the sample mass, (e) cGMP diffuses freely in OS water during the transduction time and ΔH for cGMP hydrolysis is 11.2 kcal mol$^{-1}$.
(4) Dark current shutdown during a light response should faster than $q_1$ heat evolution, as predicted by eq. (10).
(5) Inhibitors of the cGMP PDEase should increase the dark level of cGMP, slow its hydrolysis in light, and raise the total $q_1$ heat.

The properties of $q_1$ agree with the predictions (1), (2) and (5) but not (3–4). The slowing effect of IBMX suggests that PDEase activity underlies $q_1$. If $q_1$ is not due to cGMP splitting, one must explain the lack of heat expected from prediction (2). Neither the present heat measurements nor the patch clamp results conform to the larger light-induced changes in acid-extractable cGMP seen in rods. The discrepancy could be explained if cGMP's free energy of hydrolysis were conserved in some coupled reaction, or cGMP might be bound and released unchanged.

Raising intracellular [Ca$^{++}$] has long been known to suppress the dark current conductance quickly, reversibly and selectively. But even millimolar levels of divalent cations have only weak and non-selective inhibitory effects on the conductance of isolated rod membrane patches It has been suggested that Ca$^{++}$ blocks the formation of cGMP. The persistence of a normal $q_1$ when the dark current is inhibited by high external CA$^{++}$ or by ouabain argues that calcium controls the dark current in some other way in dark-adapted rods.

The cooling trend, $r_1$, which is reversed by high Ca$^{++}$ and other treatments that suppress the dark current, does not seem to be directly connected with transduction but rather with suspension during light responses of exothermic metabolic processes that sustain the dark current. $r_1$'s size suggests that the retina is normally about 1mK warmer than the ambient. The dark current itself has little heating effect since its flow only mixes two ionic solutions. $r_1$ is clearly composite.

The above example illustrates one advantageous use of the pyroelectric calorimeter of the present invention. Because of its high sensitivity, the pyroelectric calorimeter of the present invention can be used in investigating a variety of metabolic events that occur in living cells and tissues.

The invention has been described herein with reference to certain preferred embodiments. However, as obvious variations thereon will become apparent to those skilled in the art, the invention is not to be considered as limited thereto.

We claim:

1. A pyroelectric detector comprising a support member having a tapered through-hole therein, a first polyester film positioned on said support member, across said through-hole, an aluminum foil member located on an opposite side of said polyester film from said support member, a pyroelectric film located on an opposite side of said aluminum foil member from said first polyester film, at least one additional polyester film located on an opposite side of said pyroelectric film from said aluminum foil member, and two pyroelectrical leads connected to opposite sides of said pyroelectric film.

2. The pyroelectric detector of claim 1 wherein said pyroelectric film comprises a poly(vinylidene 1,1-difluoride).

3. The pyroelectric detector of claim 2 wherein said pyroelectric film comprises a poled metal-coated poly(vinylidene 1,1-difluoride).

4. The pyroelectric detector of claim 3 wherein said metal coating on said poly(vinylidene 1,1-difluoride) is selected from the group consisting of nickel and aluminum.

5. The pyroelectric detector of claim 1 wherein said at least one additional polyester film include through-holes therein through which said two electrical leads pass.

6. The pyroelectric detector of claim 5 wherein said at least one additional polyester film comprises two polyester films.

7. The pyroelectric detector of claim 1 wherein one of said two electrical leads is connected to an area of silver paint located on said first polyester film which silver paint contacts said aluminum foil member.

8. The pyroelectric detector of claim 1 wherein said polyester films, said aluminum foil member and said pyroelectric film are fixed to their respective adjacent elements by a cyanoacrylate adhesive.

* * * * *